United States Patent [19]

Uno et al.

[11] Patent Number: 4,686,221
[45] Date of Patent: Aug. 11, 1987

[54] QUINOLINECARBOXYLIC ACID COMPOUNDS AND ANTIMICROBIAL AGENT CONTAINING THE SAME

[75] Inventors: Toshio Uno, Daito; Masahiro Taguchi, Hirakata; Toshimi Okuno, Osaka; Hirosato Kondo, Suita; Mikio Sotomura, Kobe; Goro Tsukamoto, Toyonaka, all of Japan

[73] Assignee: Kanebo, Ltd., Tokyo, Japan

[21] Appl. No.: 913,382

[22] Filed: Sep. 30, 1986

[30] Foreign Application Priority Data

Oct. 1, 1985 [JP] Japan ................... 60-219379
May 2, 1986 [JP] Japan ................... 61-102568

[51] Int. Cl.⁴ ................ A61K 31/495; C07D 401/04
[52] U.S. Cl. ........................ 514/254; 544/363; 544/383; 544/386; 546/156; 546/153
[58] Field of Search ................ 544/363; 514/254

[56] References Cited

U.S. PATENT DOCUMENTS 4,522,819 6/1985 Fox, Jr. et al. ................... 544/363
4,559,341 12/1985 Petersen et al. ................... 544/363

Primary Examiner—Richard L. Raymond
Assistant Examiner—James H. Turnipseed
Attorney, Agent, or Firm—Wegner & Bretschneider

[57] ABSTRACT

Novel compounds of the formula:

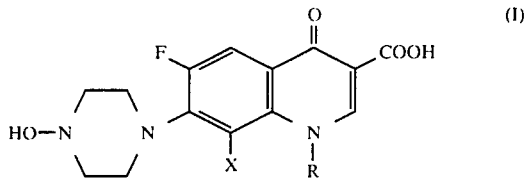

wherein R is ethyl, 2-fluoroethyl or cyclopropyl, and X is hydrogen atom or fluorine atom, and a pharmaceutically acceptable salt thereof, which have excellent antimicrobial activities in vivo and hence are useful as an antimicrobial agent, and an antimicrobial composition containing said compound as an active ingredient, and processes for the preparation of the compounds.

12 Claims, No Drawings

QUINOLINECARBOXYLIC ACID COMPOUNDS AND ANTIMICROBIAL AGENT CONTAINING THE SAME

This invention relates to novel quinolinecarboxylic acid compounds and an antimicrobial agent containing said compound as an active ingredient. More particularly, it relates to 6-fluoro-1,4-dihydro-7-(4-hydroxypiperazin-1-yl)-4-oxoquinoline-3-carboxylic acid compounds of the formula:

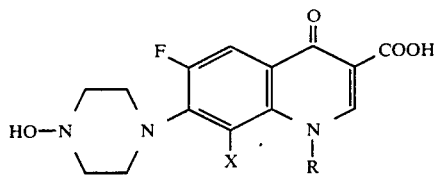
(I)

wherein R is ethyl, 2-fluoroethyl or cyclopropyl, and X is a hydrogen atom or fluorine atom, and a pharmaceutically acceptable salt thereof, and an antimicrobial agent containing said compound as an active ingredient.

PRIOR ART

Numerous quinolinecarboxylic acid compounds have hitherto been known. Among them, the following compounds are known to have particularly high antimicrobial activities (these compounds are referred to as Reference Compounds A, B, C, D, and E).

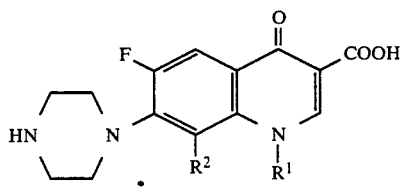
(I)

| Reference Compound | $R^1$ | $R^2$ | Literatures |
|---|---|---|---|
| A | $-C_2H_5$ | H | U.S. Pat. No. 4146719 |
| B (HCl salt) | $-\triangleleft$ | H | E.P. 78362 |
| C (HCl salt) | $-C_2H_5$ | F | G.B. Patent 2057440 |
| D (HCl salt) | $-CH_2CH_2F$ | F | U.S. Pat. No. 4398029 |
| E (HCl salt) | $-\triangleleft$ | F | U.S. Pat. No. 4556658 |

These known compounds are related to the compounds of this invention in that they contain the piperazinyl group at 7-position of the quinolinecarboxylic acid nucleus. It is assumed that the piperazinyl group will have a great effect on the exhibition of the antimicrobial activities.

However, these quinolinecarboxylic acid compounds having a piperazinyl group at 7-position (hereinafter referred to as 7-piperazinylquinolinecarboxylic acid compound) have still insufficient antimicrobial activities in vivo, and hence, it is desirable to find other compounds having superior antimicrobial activities in vivo.

BRIEF SUMMARY OF THE INVENTION

The present inventors have made studies to find novel quinolinecarboxylic acid compounds having improved antimicrobial activities in vivo by replacing the piperazinyl group at 7-position by various substituted piperazinyl groups, and have found that introduction of 4-hydroxypiparzinyl group is effective for improvement of the antimicrobial activities in vivo.

An object of the invention is to provide novel quinolinecarboxylic acid compounds having improved antimicrobial activities in vivo. Another object of the invention is to provide novel 4-hydroxypiperazinyl-quinolinecarboxylic acid compounds and a pharmaceutically acceptable salt thereof. A further object of the invention is to provide an antimicrobial agent containing as an active ingredient the novel 4-hydroxypiperazinylquinolinecarboxylic acid compound or a pharmaceutically acceptable salt thereof. These and and other objects and advantages of the invention will be apparent to skilled person from the following description.

DETAILED DESCRIPTION OF THE INVENTION

The compounds of this invention have the formula (I) as set forth hereinbefore, and the novel quinolinecarboxylic acid compounds (I) and a pharmaceutically acceptable salt thereof have superior antimicrobial activities in vivo to the known 7-piperazinylquinolinecarboxylic acid compounds and have less toxicity.

Preferred specific compounds of this invention are 1-ethyl-6-fluoro-1,4-dihydro-7-(4-hydroxypiperazin-1-yl)-4-oxoquinoline-3-carboxylic acid, 1-cyclopropyl-6-fluoro-1,4-dihydro-7-(4-hydroxypiperazin-1-yl)-4-oxoquinoline-3-carboxylic acid, 1-ethyl-6,8-difluoro-1,4-dihydro-7-(4-hydroxypiperazin-1-yl)-4-oxoquinoline-3-carboxylic acid, 6,8-difluoro-1-(2-fluoroethyl)-1,4-dihydro-7-(4-hydroxypiperazin-1-yl)-4-oxoquinoline-3-carboxylic acid, and 1-cyclopropyl-6,8-difluoro-1,4-dihydro-7-(4-hydroxypiperazin-1-yl)-4-oxoquinoline-3-carboxylic acid.

The compounds of this invention include a pharmaceutically acceptable salt of the compounds of the formula (I). Preferred pharmaceutically acceptable salts are acid addition salts, such as hydrochloride, methanesulfonate, etc.

The compounds of this invention can be prepared by various processes, for instance, by Process A and Process B as mentioned below. Besides, the compounds of the formula (I) wherein R is ethyl or cyclopropyl and X is hydrogen atom or fluorine atom can also be prepared by Process C as mentioned hereinafter.

Process A

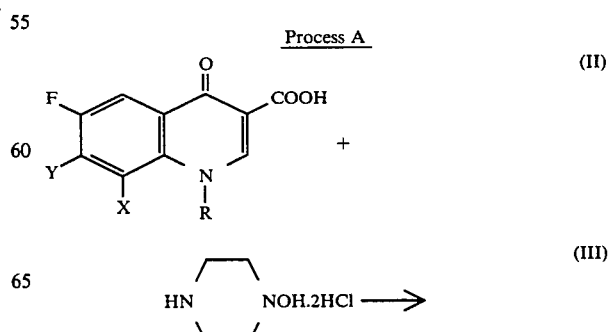

-continued

Process A

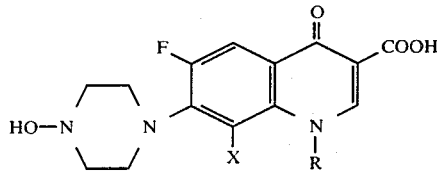

wherein R and X are as defined above, and Y is fluorine or chlorine.

The compounds (I) can be prepared by reacting a known compound (II) with an acid addition salt (e.g. dihydrochloride) of 1-hydroxypiperazine (III) in a solvent in the presence of a base. The compound (III) is usually used in an amount of 1 to 4 moles, preferably 1.2 to 3 moles, per 1 mole of the compound (II). The base is preferably a tertiary amine (e.g. triethylamine), which is usually used in an amount of 4 to 15 moles per 1 mole of the compound (II). Suitable solvents are polar solvents, such as dimethylsulfoxide, dimethylformamide, pyridine, tetrahydrofuran, acetonitrile, methanol and ethanol. The reaction is usually carried out at a temperature of 50° to 200° C., preferably 60° to 150° C., for 30 minutes to 5 hours.

The starting compound (III) used in the above Process A, i.e. the acid addition salt (e.g. dihydrochloride) of 1-hydroxypiperazine can be prepared, for example, by a process as shown in the following reaction scheme:

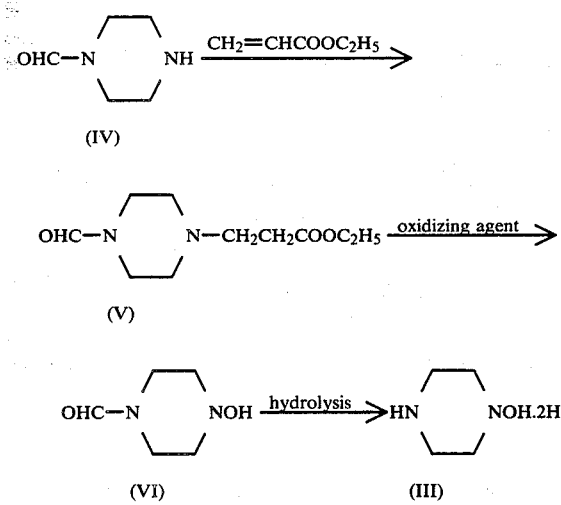

That is, 1-formylpiperazine (IV) is reacted with ethyl acrylate to give a compound (V), and the resulting compound is treated with an oxidizing agent (e.g. hydrogen peroxide) preferably in the presence of a catalyst (e.g. sodium tungstate) to give 4-hydroxy-1-formyl-piperazine (VI). The compound (VI) is hydrolyzed with hydrochloric acid to give 1-hydroxypiperazine dihydrochloride (III).

Process B

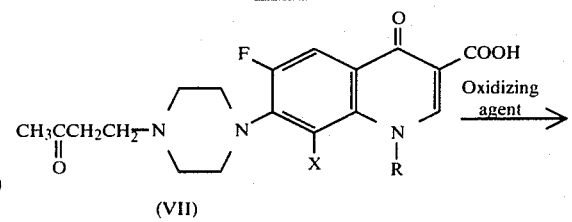

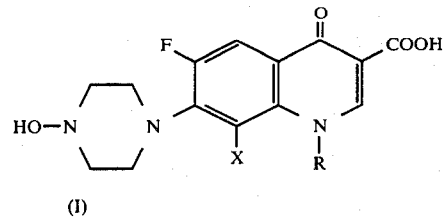

wherein R and X are as defined above.

The compounds (I) can be prepared by reacting a compound (VII) with an oxidizing agent in an organic solvent (e.g. chloroform, methanol, etc.). The oxidizing agent includes m-chloroperbenzoic acid, peracetic acid, hydrogen peroxide, and the like, which is usually used in an amount of 1.0 to 5.0 moles, preferably, 1.2 to 3.0 moles, per 1 mole of the compound (VII). The reaction is usually carried out at a temperature of 0° C. to 100° C. for 3 to 24 hours.

Among the compounds (VII) used in the above Process B, the compounds of the formula (VII) wherein R is cyclopropyl and X is hydrogen atom, and R is cyclopropyl and X is fluorine atom are known (cf. Japanese Patent First Publication Nos. 172471/1984 and 212474/1984, and U.S. Pat. No. 4,556,658). Other compounds (VII) can be prepared in the same manner as disclosed in the above references, i.e. by reacting a known 7-piperazinylquinolinecarboxylic acid compound (cf. Japanese Patent First Publication Nos. 141286/1978, 66686/1979, 47658/1980 and 30964/1981, U.S. Pat. No. 4,146,719, G. B. Pat. No. 2,057,440, and U.S. Pat. No. 4,398,029) with methyl vinyl ketone.

Process C

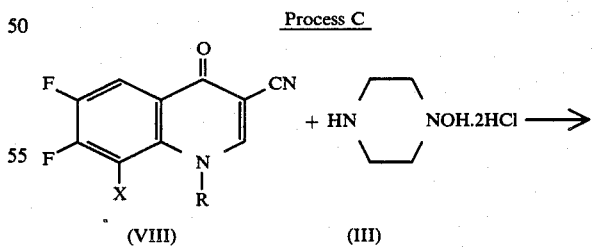

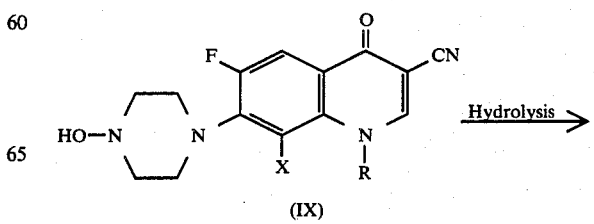

-continued

Process C

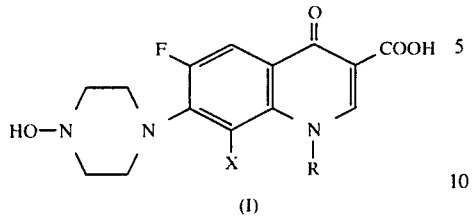

wherein R is ethyl or cyclopropyl, and X is hydrogen or fluorine.

According to Process C, firstly a 3-cyanoquinoline compound (VIII) is reacted with a 1-hydroxypiperazidine acid addition salt (e.g. dihydrochloride) (III) in a solvent in the presence of a base to give a 7-(4-hydroxypiperazin-1-yl)-3-cyanoquinoline compound (IX). In this reaction, the compound (III) is usually used in an amount of 1 to 4 moles, preferably 1.2 to 3 moles, per 1 mole of the compound (VIII). The base is preferably tertiary amines (e.g. triethylamine), which is usally used in an amount of 4 to 15 moles per 1 mole of the compound (VIII). Preferred solvent is a polar solvent, such as dimethylsulfoxide, dimethylformamide, etc. The reaction is usually carried out at a temperature of 50° to 150° C., preferably 80° to 130° C., for 1 to 8 hours.

The compound (IX) is subsequently hydrolyzed with an acid, and the resulting acid addition salt is neutralized to give the compound of the formula (I) wherein R is ethyl or cyclopropyl and X is a hydrogen atom or fluorine atom. Preferred acid used for the hydrolysis is, for example, hydrochloric acid. The reaction is usually carried out at a temperature of 70° to 100° C. for 6 to 10 hours.

The 3-cyanoquinoline compounds (VIII) used in the above Process C can be prepared, for example, by a process as shown in the following reaction scheme:

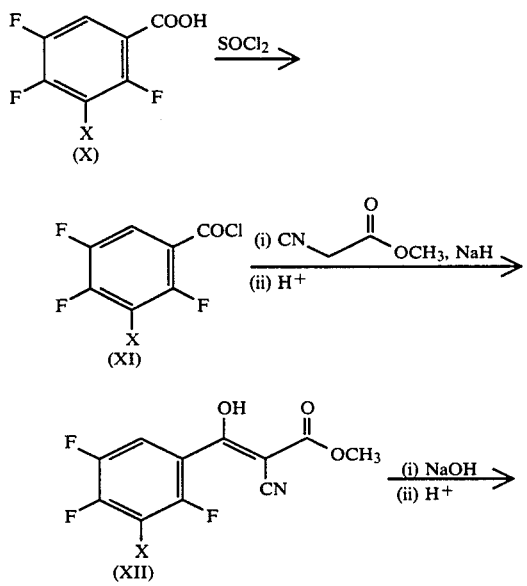

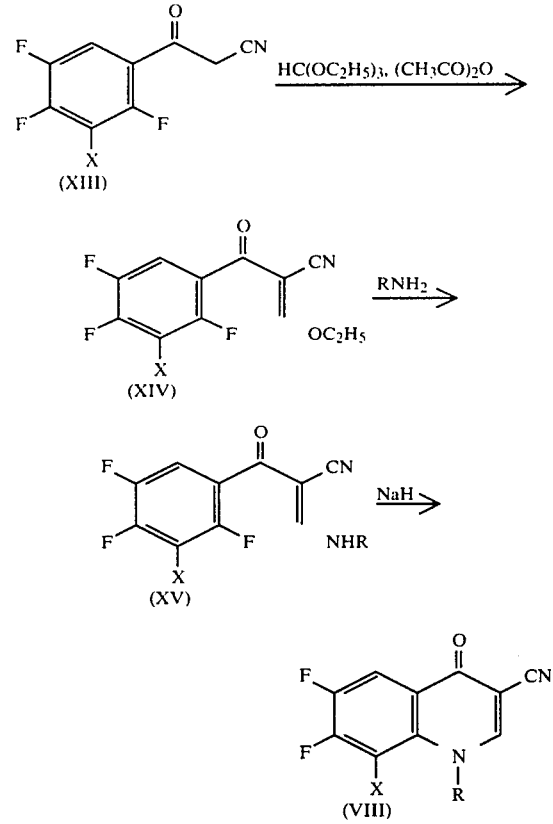

wherein R is ethyl or cyclopropyl and X is hydrogen atom or fluorine atom.

First a benzoic acid compound (X) is reacted with thionyl chloride in the presence of a catalytic amount of dimethylformamide to give an acid chloride (XI). The compound (XI) is subsequently reacted with methyl cyanoacetate in the presene of sodium hydride and then acidified with hydrochloric acid to give a compound (XII). The compound (XII) is treated with aqueous sodium hydroxide and then acidified with hydrochloric acid to give a compound (XIII). The resulting compound (XIII) is reacted with ethyl orthoformate in the presence of acetic anhydride to give a compound (XIV). The compound (XIV) is reacted with ethylamine or cyclopropylamine to give a compound (XV). The compound (XV) is finally treated with sodium hydride to give a 3-cyanoquinoline compound (VIII).

The compounds (I) of the invention as prepared by the above processes can be isolated and purified from the reaction mixture by a conventional purification method, for example, by silica gel column chromatography or recrystallization. The compounds (I) can be converted into a salt thereof by treating them with an acid or a base in a usual manner.

The compounds (I) and a pharmaceutically acceptable salt thereof are used as an antimicrobial agent by administering to animals, particularly human patients, by oral route. These compounds are usually used in conventional pharmaceutical preparations, such as tablets, granules, fine granules, powders, syrups, and the like, which are prepared by admixing with conventional pharmaceutically acceptable nontoxic carriers or diluents, such as corn starch, lactose, magnesium stearate, fine crystalline cellulose, kaolin, calcium carbonate, talc, etc., or capsules which are prepared by packing the above-menioned granules, fine granules or powders into capsules.

The dose of the compounds of this invention may vary in accordance with age and body weight of the patients and severity of diseases, and the like, but is usually in the range of 0.5 to 30 mg/kg of body weight/day, preferably 2 to 20 mg/kg of body weight/day [as the compound (I)], which may be administered once a day or may be divided into 2 to 4 times per day.

The compounds of this invention show the same as or somewhat inferior antimicrobial activities in vitro in comparison with the known 7-piperazinylquinoinecarboxylic acid compounds, but show superior antimicrobial activities in vivo to the latter. That is, according to comparative experiments, the compounds of this invention showed the same or somewhat larger MIC (minimum inhibitory concentration) in comparison with the corresponding reference compounds, but showed superior activities in the infectious protection test in mice to the latter (cf. Experiment 1, Tables 1 to 5).

Besides, the compounds of this invention show lower toxicity (cf. Experiment 2).

The pharmacological experiments are shown below.

EXPERIMENT 1: TEST OF ANTIMICROBIAL ACTIVITIES

1. Test compounds (1) Compound No. 1 of this invention: 1-Ethyl-6-fluoro-1,4-dihydro-7-(4-hydroxypiperazin-1-yl)-4-oxoquinoline-3-carboxylic acid (compound of Example 1)
(2) Reference Compound A (reference compound corresponding to Compound No. 1): 1-Ethyl-6-fluoro-1,4-dihydro-7-(piperazin-1-yl)-4-oxoquinoline-3-carboxylic acid
(3) Compound No. 2 of this invention: 1-Cyclopropyl-6-fluoro-1,4-dihydro-7-(4-hydroxypiperazin-1-yl)-4-oxoquinoline-3-carboxylic acid hydrochloride ¼ hydrate (compound of Example 2)
(4) Reference Compound B (reference compound corresponding to Compound No. 2): 1-Cyclopropyl-6-fluoro-1,4-dihydro-7-(piperazin-1-yl)-4-oxoquinoline-3-carboxylic acid hydrochloride
(5) Compound No. 3 of this invention: 1-Ethyl-6,8-difluoro-1,4-dihydro-7-(4-hydroxypiperazin-1-yl)-4-oxoquinoline-3-carboxylic acid hydrochloride (compound of Example 3)
(6) Reference Compound C (reference compound corresponding to Compound No. 3): 1-Ethyl-6,8-difluoro-1,4-dihydro-7-(piperazin-1-yl)-4-oxoquinoline-3-carboxylic acid hydrochloride
(7) Compound No. 4 of this invention: 6,8-Difluoro-1-(2-fluoroethyl)-1,4-dihydro-7-(4-hydroxypiperazin-1-yl)-4-oxoquinoline-3-carboxylic acid hydrochloride monohydrate (compound of Example 4)
(8) Reference Compound D (reference compound corresponding to Compound No. 4): 6,8-Difluoro-1-(2-fluoroethyl)-1,4-dihydro-7-(piperazin-1-yl)-4-oxoquinoline-3-carboxylic acid hydrochloride
(9) Compound No. 5 of this invention: 1-Cyclopropyl-6,8-difluoro-1,4-dihydro-7-(4-hydroxypiperazin-1-yl)-4-oxoquinoline-3-carboxylic acid hydrochloride (compound of Example 5)
(10) Reference Compound E (reference compound corresponding to Compound No. 5): 1-Cyclopropyl-6,8-difluoro-1,4-dihydro-7-(piperazin-1-yl)-4-oxoquinoline-3-carboxylic acid hydrochloride 2. Test microorganisms

*Staphylococcus aureus* IID 803
*Escherichia coli* KC-14

3. Method (1) Measurement of antibacterial activity in vitro (minimum inhibitory concentration: MIC):

The test compounds were each dissolved in 0.1N aqueous potassium hydroxide or sterilized distilled water and diluted with sterilized distilled water to give a standard solution (concentration: 1,000 μg/ml). The test was carried out by a method as appointed by Japan Society of Chemotherapy [cf. Chemotherapy, 29, 76–79 (1981) (TOKYO)].

(2) Measurement of antibacterial activity in vivo (effect against systemic infection: $ED_{50}$):

The test microorganism was cultured by stationary culture in an agar medium (Trypto-Soya Agar "Nissui", manufactured by Nissui Seiyaku K.K., Japan) at 37° C. for 16 to 18 hours. The culture was diluted with PBS (Dulbecco's phosphate buffered saline) and then was mixed with an equiamount of 10% (W/V) mucin (BACTO MUCIN BACTERIOLOGICAL, manufactured by Difco Co.). The mixture thus prepared was intraperitoneally inoculated to fasted ddY male mice (4 weeks age, weighing 18–20 g, one group: 5 mice) in a dose of 0.5 ml. The inoculum size was $1.3 \times 10^7$ CFU/mouse in case of *S. aureus* IID 803, and $9.7 \times 10^3$ CFU/mouse in case of *E. coli* KC-14. One hour after the infection, the test compound suspended in 0.5% (W/V) aqueous sodium carboxymethyl cellulose solution was orally administered to the infected mice (in the case of Reference Compound B, it was orally administered in the form of a solution in sterilized distilled water).

The mice were daily observed for one week, and from the survival number of mice after one week, the 50% effective dose ($ED_{50}$) was calculated by the Weil method.

4. Results

The test results are shown in Tables 1 to 5.

EXPERIMENT 2: ACUTE TOXICITY ($LD_{50}$)

1. Test compounds

The same as in Experiment 1.

2. Method

Each test compound was suspended in 0.5% (W/V) aqueous sodium carboxymethyl cellulose solution, and the suspension was orally administered to ddY male mice (5 weeks age, weighing 20–25 g, one group: 10 mice) (in case of Reference Compound B, it was orally administered in the form of a solution in sterilized distilled water). The number of dead mice during 2 weeks after administration was counted, and the acute toxicity ($LD_{50}$) was calculated by Weil method.

3. Results

The test results are shown in Tables 1 to 5.

TABLE 1

Structure: 6-fluoro-7-(4-Z-piperazin-1-yl)-1-ethyl-4-oxo-1,4-dihydroquinoline-3-carboxylic acid

| Test compounds | | Antibacterial activity | | | | Acute toxicity |
|---|---|---|---|---|---|---|
| Compd. | | S. aureus IID 803 | | E. coli KC-14 | | LD$_{50}$ |
| No. | Z | MIC*[1] | ED$_{50}$*[2] | MIC*[1] | ED$_{50}$*[2] | (mg/kg) |
| Compd. No. 1 | OH | 1.56 | 187 | 0.39 | 1.92 | >4,000 |
| Ref. Compd. A | H | 1.56 | 225 | 0.20 | 5.82 | >4,000 |

*[1]Minimum inhibitory concentration (μg/ml)
*[2]50% effective dose (mg/kg)

TABLE 2

Structure: 6-fluoro-7-(4-Z-piperazin-1-yl)-1-cyclopropyl-4-oxo-1,4-dihydroquinoline-3-carboxylic acid · HCl

| Test compounds | | Antibacterial activity | | | | Acute toxicity |
|---|---|---|---|---|---|---|
| Compd. | | S. aureus IID 803 | | E. coli KC-14 | | LD$_{50}$ |
| No. | Z | MIC*[1] | ED$_{50}$*[2] | MIC*[1] | ED$_{50}$*[2] | (mg/kg) |
| Compd. No. 2 | OH | 0.78 | 17.7 | 0.025 | 0.37 | >4,000 |
| Ref. Compd. B | H | 0.78 | 46.7 | 0.0125 | 0.84 | >4,000 |

*[1]Minimum inhibitory concentration (μg/ml)
*[2]50% effective dose (mg/kg)

TABLE 3

Structure: 6,8-difluoro-7-(4-Z-piperazin-1-yl)-1-ethyl-4-oxo-1,4-dihydroquinoline-3-carboxylic acid · HCl

| Test compounds | | Antibacterial activity | | | | Acute toxicity |
|---|---|---|---|---|---|---|
| Compd. | | S. aureus IID 803 | | E. coli KC-14 | | LD$_{50}$ |
| No. | Z | MIC*[1] | ED$_{50}$*[2] | MIC*[1] | ED$_{50}$*[2] | (mg/kg) |
| Compd. No. 3 | OH | 0.78 | 26.8 | 0.20 | 0.84 | >4,000 |
| Ref. Compd. C | H | 0.78 | 40.3 | 0.10 | 1.46 | 1,072 |

*[1]Minimum inhibitory concentration (μg/ml)
*[2]50% effective dose (mg/kg)

TABLE 4

Structure: 6,8-difluoro-7-(4-Z-piperazin-1-yl)-1-(2-fluoroethyl)-4-oxo-1,4-dihydroquinoline-3-carboxylic acid · HCl

| Test compounds | | Antibacterial activity | | | | Acute toxicity |
|---|---|---|---|---|---|---|
| Compd. | | S. aureus IID 803 | | E. coli KC-14 | | LD$_{50}$ |
| No. | Z | MIC*[1] | ED$_{50}$*[2] | MIC*[1] | ED$_{50}$*[2] | (mg/kg) |
| Compd. No. 4 | OH | 1.56 | 107 | 0.39 | 1.46 | >4,000 |
| Ref. Compd. D | H | 1.56 | 123 | 0.20 | 5.82 | — |

*[1]Minimum inhibitory concentration (μg/ml)
*[2]50% effective dose (mg/kg)

TABLE 5

Structure: 6,8-difluoro-7-(4-Z-piperazin-1-yl)-1-cyclopropyl-4-oxo-1,4-dihydroquinoline-3-carboxylic acid · HCl

| Test compounds | | Antibacterial activity | | | | Acute toxicity |
|---|---|---|---|---|---|---|
| Compd. | | S. aureus IID 803 | | E. coli KC-14 | | LD$_{50}$ |
| No. | Z | MIC*[1] | ED$_{50}$*[2] | MIC*[1] | ED$_{50}$*[2] | (mg/kg) |
| Compd. No. 5 | OH | 0.39 | 3.84 | 0.05 | 0.19 | >4,000 |
| Ref. Compd. E | H | 0.20 | 5.07 | 0.0125 | 0.28 | 1,414 |

*[1]Minimum inhibitory concentration (μg/ml)
*[2]50% effective dose (mg/kg)

As is clear from the above experimental results, the compounds of this invention are effective as an antimicrobial agent with high safety.

This invention is illustrated by the following Preparations and Examples.

PREPARATION 1

Preparation of 1-hydroxypiperazine hydrochloride

1-Hydroxypiperazine dihydrochloride is prepared according to the following procedures from (1) to (3).

(1) Preparation of 4-ethoxycarbonylethyl-1-formylpiperazine:

Ethyl acrylate (326 g) and chloroform (2 liters) are added to 1-formylpiperazine (320 g) and the mixture is stirred at room temperature for 3 days. The solvent is evaporated under reduced pressure to yield crude 4-ethoxycarbonylethyl-1-formylpiperazine (580 g) as an orange oil.

NMR (CDCl$_3$) δ: 1.25 (3H, t, J=8 Hz), 2.25–2.90 (8H, m), 3.20–3.70 (4H, m), 4.03 (2H, q, J=8 Hz), 8.01 (1H, s)

(2) Preparation of 1-formyl-4-hydroxypiperazine:

The crude 4-ethoxycarbonylethyl-1-formylpiperazine (114 g) prepared as described above is dissolved in water (500 ml) and sodium tungstate dihydrate (7.25 g) is added to the solution. At a temperature of 30°–35° C., 31% hydrogen peroxide (82 ml) is added dropwise to the solution and the mixture is stirred for one hour. The reaction mixture is stirred for 3 hours at room temperature and for another 5 hours at a temperature of 50°–55° C. The resulting reaction mixture is then shaken with ethyl acetate (300 ml). The aqueous layer is evaporated under reduced pressure to remove water to yield a dark brown oil. The oil is applied to a silica gel column chromatography for the purification (2 kg of silica gel, eluent; chloroform:methanol = 10:1) and then is recrystallized from ethyl acetate to give 1-formyl-4-hydroxypiperazine (38.2 g), m.p. 118°–124° C.

Elementary analysis for $C_5H_{10}N_2O_2$: Calcd. (%): C, 46.14; H, 7.75; N, 21.52; Found (%): C, 46.12; H, 7.57; N, 21.55.

(3) Preparation of 1-hydroxypiperazine dihydrochloride:

To 1-formyl-4-hydroxypiperazine (5.0 g) is added 3N hydrochloric acid (50 ml) and the mixture is heated at 77°–87° C. with stirring for 20 minutes and water is removed from the mixture under reduced pressure to yield a pale yellow residue. After washing with ethanol, the residue is crystallized from a mixture of water and ethanol to give 1-hydroxypiperazine dihydrochloride (5.0 g) as light brown prisms, m.p. 164°–175° C. (decomposition).

Mass spectral analysis: m/e: 102 ($M^+$), 85 ($M^+$ —OH).

IR (KBr) $\nu$ max (cm$^{-1}$): 3240, 3010, 2720, 1558, 1501, 1452, 1448, 1433, etc.

NMR (DMSO-$d_6$) δ: 3.1–3.8 (m), 9.4–10.1 (m).

Elementary analysis for $C_4H_{10}N_2O \cdot 2HCl$: Calcd. (%): C, 27.44; H, 6.91; N, 16.00; Found (%): C, 27.18; H, 6.96; N, 15.97.

PREPARATION 2

Preparation of 1-ethyl-6-fluoro-1,4-dihydro-7-[4-(3-oxobutyl)piperazin-1-yl]-4-oxoquinoline-3-carboxylic acid 1-Ethyl-6-fluoro-1,4-dihydro-7-(piperazin-1-yl)-4-oxoquinoline-3-carboxylic acid (5 g), which is prepared by the procedure described in Japanese Patent First Publication No. 141286/1978, is suspended in chloroform (150 ml). To the suspension is added methyl vinyl ketone (2 g) and the mixture is stirred at room temperature for 5 hours. When the reaction is completed, the reaction mixture is evaporated under vacuum to remove the solvent and the resulting residue is recrystallized from a mixture of chloroform and ethanol to yield the title compound (4.2 g) as white needles, m.p. 187°–193° C. (decomposition).

IR (KBr) $\nu$ max (cm$^{-1}$): 3050, 2850, 1730, 1718, 1632, 1530, 1448, 1265, etc.

NMR (CDCl$_3$) δ: 1.60 (3H, t, J=7 Hz), 2.10 (3H, s), 2.60–2.80 (8H, m), 3.24–3.44 (4H, m), 4.34 (2H, q, J=7 Hz), 6.84 (1H, d, J=8 Hz), 8.02 (1H, d, J=13.5 Hz), 8.64 (1H, s), 14.82 (1H, bs).

Elementary analysis for $C_{20}H_{24}FN_3O_4$: Calcd. (%): C, 61.68; H, 6.21; N, 10.79; Found (%): C, 61.63; H, 6.23; N, 10.74.

PREPARATION 3

Preparation of 1-cyclopropyl-3-cyano-1,4-dihydro-4-oxo-6,7,8-trifluoroquinoline

1-Cyclopropyl-3-cyano-1,4-dihydro-4-oxo-6,7,8-trifluoroquinoline is prepared according to the following precedures from (1) to (5).

(1) Preparation of methyl 2-cyano-3-hydroxy-3-(2,3,4,5-tetrafluorophenyl)acrylate:

Dimethylformamide (0.6 ml) is added to a mixture of 2,3,4,5-tetrafluorobenzoic acid (100 g) and thionyl chloride (135 ml), and the mixture is heated under reflux with stirring for 7 hours. The reaction mixture is condensed under vacuum to yield crude 2,3,4,5-tetrafluorobenzoyl chloride as a pale yellow oily residue (110.5 g).

Methyl cyanoacetate (51.1 g) is added dropwise to a suspension of sodium hydride (43.3 g, in oil, 55–65 w/w %) in dry tetrahydrofuran (600 ml) while maintaining the internal temperature between 15° C. and 20° C. on an ice bath. To the reaction mixture is added dropwise the crude 2,3,4,5-tetrafluorobenzoyl chloride (110.5 g) as obtained above, and the mixture is stirred while maintaining the internal temprature as above. After 30 minutes, methylene chloride is added to the reaction mixture and the reaction product is extracted with 3% aqueous sodium bicarbonate. The extract is then washed with methylene chloride to remove the remaining methyl cyanoacetate. The extract is acidified with conc. HCl and the resulting precipitate is filtered and washed with dil. HCl to afford methyl 2-cyano-3-hydroxy-3-(2,3,4,5-tetrafluorophenyl)acrylate (122.2 g) as pale yellow crystals, m.p. 71°–73° C.

IR (KBr) $\nu$ max (cm$^{-1}$): 3086, 2238, 1680, 1597, 1530, 1488, 1446, 1390, 1356, 1313, 1274, 1240, 1200, etc.

NMR (CDCl$_3$) δ: 4.00 (3H, s), 7.14–7.43 (1H, m), 13.74 (bs).

Elementary analysis for $C_{11}H_5F_4NO_3$: Calcd. (%): C, 48.01; H, 1.83; N, 5.09; Found (%): C, 47.99; H, 2.09; N, 5.15.

(2) Preparation of 2-(2,3,4,5-tetrafluorobenzoyl)acetonitrile:

Methyl 2-cyano-3-hydroxy-3-(2,3,4,5-tetrafluorophenyl)acrylate (75.1 g) is added to a solution of sodium hydroxyde (110 g) in water (1.1 liter) and the mixture is stirred at room temperature for 26 hours. To the reaction mixture is added ice (1.3 Kg) and conc. HCl. After 1 hour, the precipitate is filtered and washed with dil. HCl to yield 2-(2,3,4,5-tetrafluorobenzoyl)acetonitrile (52.7 g) as a light cream colored powder, m.p. 60°–61° C.

IR (KBr) $\nu$ max (cm$^{-1}$): 3076, 2966, 2942, 2930, 2264, 1703, 1638, 1538, 1525, 1483, 1386, 1372, 1323, 1293, 1197, etc.

NMR (CDCl$_3$) δ: 4.06 (2H, d, J=3 Hz), 7.40–7.78 (1H, m).

Elementary analysis for $C_9H_3F_4NO$: Calcd. (%): C, 49.79; H, 1.39; N, 6.45; Found (%): C, 49.78; H, 1.24; N, 6.62.

(3) 3-Ethoxy-2-(2,3,4,5-tetrafluorobenzoyl)acrylonitrile:

A mixture of 2-(2,3,4,5-tetrafluorobenzoyl)acetonitrile (13.1 g), ethyl orthoformate (13.4 g) and acetic anhydride (15.4 g) is heated at 100° C. with stirring for 3 hours. The reaction mixture is concentrated under vacuum to yield an orange brownish oily residue. When the oily residue is allowed to stand at room temperature, it crystallizes slowly. The resulting crystals are collected and washed successively with a 2:1 mixture of hexane and ethyl acetate, and a 5:1 mixture of hexane and ethyl acetate to give 3-ethoxy-2-(2,3,4,5-tetrafluorobenzoyl)acrylonitrile (14.5 g) as light orange crystals, m.p. 99°–101° C.

IR (KBr) νmax (cm$^{-1}$): 3042, 2236, 1665, 1601, 1528, 1485, 1384, 1372, 1358, 1332, etc.

NMR (CDCl$_3$) δ: 1.50 (3H, t, J=8 Hz), 4.45 (2H, q, J=8 Hz), 7.02–7.31 (1H, m), 8.05 (1H, s).

Elementary analysis for $C_{12}H_7F_4NO_2$: Calcd. (%): C, 52.76; H, 2.58; N, 5.13; Found (%): C, 52.76; H, 2.42; N, 5.27.

(4) Preparation of 3-cyclopropylamino-2-(2,3,4,5-tetrafluorobenzoyl)acrylonitrile:

A solution of cyclopropylamine (3.3 g) in chloroform (20 ml) is added dropwise to a solution of 3-ethoxy-2-(2,3,4,5-tetrafluorobenzoyl)acrylonitrile (14.0 g) in chloroform (50 ml) with maintaining the internal temperature between 6° C. and 8° C. by using an ice bath. The mixture is allowed to stand overnight at room temperature and then concentrated under vacuum to yield an orange oily residue. The oily residue is dissolved in ethanol and the ethanol is removed in vacuum to afford a crystalline residue. The residue is dissolved in hexane and washed with a 20:1 mixture of hexane and ethanol to yield 3-cyclopropylamino-2-(2,3,4,5-tetrafluorobenzoyl)acrylonitrile (12.6 g) as pale yellow prisms, m.p. 88°–89° C.

IR (KBr) ν max (cm$^{-1}$): 3244, 2208, 1653, 1590, 1529, 1482, 1423, 1396, 1372, 1315, etc.

NMR (CDCl$_3$) δ: 0.72–1.14 (4H, m), 2.84–3.18 (1H, m), 6.96–7.30 (1H, m), 7.64 and 8.10 [1H, (dd, J=14 Hz, J<1 Hz), (dd, J=14.5 Hz, J<1 Hz); the proton at 3-position shows 2 signals owing to mixture of geometrical isomers], 10.76 (bs).

Elementary analysis for $C_{13}H_8F_4N_2O$: Calcd. (%): C, 54.94; H, 2.84; N, 9.86; Found (%): C, 55.13; H, 2.73; N, 10.02.

(5) Preparation of 1-cyclopropyl-3-cyano-1,4-dihydro-4-oxo-6,7,8-trifluoroquinoline:

A solution of 3-cyclopropylamino-2-(2,3,4,5-tetrafluorobenzoyl)acrylonitrile (12.0 g) in dioxane (60 ml) is added dropwise to a suspension of sodium hydride (1.9 g, in oil, 55–65 w/w%) in dioxane (40 ml) while maitainig the internal temperature between 16° C. and 18° C. on an ice bath. The mixture is stirred for 6 hours with heating while keeping the internal temperature around 45° C. The reaction mixture is poured into hexane (300 ml), and the resulting precipitate is filtered and washed with hexane and water to yield 1-cyclopropyl-3-cyano-1,4-dihydro-4-oxo-6,7,8-trifluoroquinoline (10.2 g) as a colorless powder, m.p. 217°–218° C.

IR (KBr) ν max (cm$^{-1}$): 3066, 3050, 2228, 1613, 1569, 1519, 1481, 1400, 1343, 1322, 1299, 1255, etc.

NMR (CDCl$_3$) δ: 1.16–1.46 (4H, m), 3.80–4.12 (1H, m), 7.92–8.15 (1H, m), 8.20 (1H, s).

Elementary analysis for $C_{13}H_7F_3N_2O$: Calcd. (%): C, 59.10; H, 2.67; N, 10.60; Found (%): C, 59.21; H, 2.55; N, 10.66.

EXAMPLE 1

Preparation of 1-ethyl-6-fluoro-1,4-dihydro-7-(4-hydroxypiperazin-1-yl)-4-oxoquinoline-3-carboxylic acid 1-Ethyl-6-fluoro-1,4-dihydro-7-[4-(3-oxobutyl)piperazin-1-yl]-4-oxoquinoline-3-carboxylic acid (4.6 g), which is prepared in Preparation 2, is dissolved in chloroform (150 ml). m-Chloroperbenzoic acid (2.44 g) is added to the solution with ice cooling, followed by stirring at room temperature for 5 hours. The reaction mixture is concentrated under vacuum to approximately half of the initial volume, and the resulting precipitate is filtered and recrystallized from a mixture of dimethylformamide and water to yield the title compound (2.41 g) as pale yellow needles, m.p. 260°–264° C. (decomposition) (which starts to color brown at around 220° C.).

IR (KBr) ν max (cm$^{-1}$): 1725, 1629, 1502, 1468, 1438, 1402, 1382, 1300, 1256, etc.

NMR (DMSO-d$_6$) δ: 1.44 (3H, t, J=7 Hz), 2.50–3.90 (8H, m), 4.60 (2H, q, J=7 Hz), 7.16 (1H, d, J=8 Hz), 7.70 (1H, d, J=14 Hz), 8.18 (1H, s), 8.88 (1H, s), 15.04 (1H, bs).

Elementary analysis for $C_{16}H_{18}FN_3O_4$: Calcd. (%): C, 57.31; H, 5.41; N, 12.53; Found (%): C, 57.47; H, 5.37; N, 12.68.

EXAMPLE 2

Preparation of 1-cyclopropyl-6-fluoro-1,4-dihydro-7-(4-hydroxypiperazin-1-yl)-4-oxoquinoline-3-carboxylic acid 1-Cyclopropyl-6-fluoro-1,4-dihydro-4-oxo-7-[4-(3-oxobutyl)piperazin-1-yl]quinoline-3-carboxylic acid (6.8 g), which is prepared according to the procedure described in Japanese Patent First Publication No. 172471/1984, is dissolved in chloroform (100 ml). m-Chloroperbenzoic acid (3.5 g) is added to the mixture, followed by stirring at room temperature overnight. After the solvent is evaporated, a 1:3 mixture of ethyl acetate and chloroform is added to the resulting residue and the mixture is stirred with ice cooling for 1 hour. The insoluble substance is filtered and then recrystallized from a mixture of dimethylformamide and water to afford 1-cyclopropyl-6-fluoro-1,4-dihydro-7-(4-hydroxypiperazin-1-yl)-4-oxoquinoline-3-carboxylic acid (3.1 g) as pale yellow needles, m.p. 261°–265° C. (decomposed with foaming) (which starts to color at around 235° C.).

IR (KBr) ν max (cm$^{-1}$): 1725, 1637, 1506, 1499, 1468, 1380, 1339, 1298, 1255, etc.

NMR (DMSO-d$_6$) δ: 1.05–1.50 (4H, m), 2.40–4.00 (9H, m), 7.55 (1H, d, J=8 Hz), 7.86 (1H, d, J=14 Hz), 8.22 (1H, s), 8.62 (1H, s), 14.99 (1H, s).

Elementary analysis for $C_{17}H_{18}FN_3O_4$: Calcd. (%): C, 58.79; H, 5.22; N, 12.10; Found (%): C, 58.76; H, 5.23; N, 12.21.

The above compound (2.0 g) is dissolved in 3N HCl (11 ml) with heating. This mixture is cooled to room temperature. The resulting crystals are filtered and washed with ethanol to afford 1-cyclopropyl-6-fluoro-1,4-dihydro-7-(4-hydroxypiperazin-1-yl)-4-oxoquinoline-3-carboxylic acid hydrochloride (1.8 g) as pale yellow needles, m.p. 222°–226° C. (decomposition).

IR (KBr) ν max (cm$^{-1}$): 3375, 2800, 2340, 2160, 1710, 1635, 1510, 1470, 1265, etc.

NMR (DMSO-d$_6$) δ: 1.10–1.48 (4H, m), 3.30–4.10 (9H, m), 7.56 (1H, d, J=8 Hz), 7.82 (1H, d, J=13.5 Hz), 8.06 (1H, s), 8.58 (1H, s), 15.04 (1H, bs).

Elementary analysis for $C_{17}H_{18}FN_3O_4 \cdot HCl \cdot \frac{1}{4}H_2O$: Calcd. (%): C, 52.58; H, 5.06; N, 10.82; Found (%): C, 52.56; H, 5.26; N, 10.76.

EXAMPLE 3

Preparation of
1-ethyl-6,8-difluoro-1,4-dihydro-7-(4-hydroxypiperazin-1-yl)-4-oxoquinoline-3-carboxylic acid 1-Hydroxypiperazine dihydrochloride (3.94 g) (which is prepared in Preparation 1), triethylamine (21 ml) and dimethylsulfoxide (30 ml) are added to 1-ethyl-6,7,8-trifluoro-1,4-dihydro-4-oxoquinoline-3-carboxylic acid (4.07 g), which is prepared according to the procedure described in Japanese Patent First Publication No. 30964/1981, and the mixture is heated at 100° C. for 30 minutes. After cooling to room temperature, water (200 ml) is added to the mixture and the pH is adjusted to 7.0 with dil. HCl. The precipitated crystals are filtered, washed with water and dried. The product is recrystallized from a mixture of dimethylformamide and water to yield 1-ethyl-6,8-difluoro-1,4-dihydro-7-(4-hydroxypiperazin-1-yl)-4-oxoquinoline-3-carboxylic acid (4.3 g) as pale yellow needles, m.p. 253°–260° C. (decomposed with foaming) (which starts to color brown at around 234° C.).

IR (KBr) $\nu$ max (cm$^{-1}$): 3060, 2960, 2850, 1727, 1614, 1555, 1511, 1491, 1471, 1452, etc.

NMR (DMSO-d$_6$) $\delta$: 1.48 (3H, t, J=6 Hz), 2.40–3.80 (8H, m), 4.40–4.80 (2H, m), 7.80 (1H, dd, J=12 Hz, J=2 Hz), 8.22 (1H, s), 8.86 (1H, s), 14.61 (1H, bs)

Elementary analysis for $C_{16}H_{17}F_2N_3O_4$: Calcd. (%): C, 54.39; H, 4.85; N, 11.85; Found (%): C, 54.29; H, 4.77; N, 11.93.

The above compound (3.0 g) is dissolved in a mixture of dimethyformamide (75 ml) and 3N HCl (15 ml) with heating. The mixture is cooled to room temperature, and resulting crystals are filtered and washed with ethanol to give 1-ethyl-6,8-difluoro-1,4-dihydro-7-(4-hydroxypiperazin-1-yl)-4-oxoquinoline-3-carboxylic acid hydrochloride (3.1 g) as pale yellow needles, m.p. 252°–265° C. (decomposition).

IR (KBr) $\nu$ max (cm$^{-1}$): 3040, 1716, 1615, 1608, 1540, 1518, 1480, 1450, etc.

NMR (DMSO-d$_6$) $\delta$: 1.48 (3H, t, J=7 Hz), 3.10–4.10 (8H, m), 4.40–4.80 (2H, m), 7.88 (1H, dd, J=11 Hz, J=2 Hz), 8.83 (1H, s).

Elementary analysis for $C_{17}H_{17}F_2N_3O_4$·HCl: Calcd. (%): C, 50.82; H, 4.51; N, 10.46; Found (%): C, 50.81; H, 4.52; N, 10.38.

EXAMPLE 4

Preparation of
6,8-difluoro-1-(2-fluoroethyl)-1,4-dihydro-7-(4-hydroxypiperazin-1-yl)-4-oxoquinoline-3-carboxylic acid 1-Hydroxypiperazine dihydrochloride (1.03 g), triethylamine (35.6 g) and dimethylformamide (85 ml) are added to 6,7,8-trifluoro-1-(2-fluoroethyl)-1,4-dihydro-4-oxoquinoline-3-carboxylic acid (8.5 g), which is prepared by the procedure described in Japanese Patent First Publication No. 30964/1981, and the mixture is stirred for 1.5 hours at 100°–105° C. After cooling to room temperature, the reaction mixture is poured into ice-water (500 ml) and the pH is adjusted to 7.0 with 50% aqueous acetic acid. The resulting precipitate is filtered, washed with water and then recrystallized from dimethylformamide. Ethanol (100 ml) is added to the resulting pale yellow needles and the mixture is refluxed for 1.5 hours. After cooling the mixture to room temperature, the insoluble substance is filtered to yield 6,8-difluoro-1-(2-fluoroethyl)-1,4-dihydro-7-(4-hydroxypiperazin-1-yl)-4-oxoquinoline-3-carboxylic acid (3.7 g) as pale yellow needles, m.p. 220°–229° C. (decomposition).

IR (KBr) $\nu$ max (cm$^{-1}$): 3050, 2950, 2850, 1718, 1624, 1555, 1513, 1478, etc.

NMR (DMSO-d$_6$) $\delta$: 2.40–3.80 (8H, m), 4.50–5.30 (4H, m), 7.86 (1H, dd, J=12 Hz, J=2 Hz), 8.21 (1H, s), 8.83 (1H, s), 14.40 (1H, bs).

Elementary analysis for $C_{16}H_{16}F_3N_3O_4$: Calcd. (%): C, 51.75; H, 4.34; N, 11.32; Found (%): C, 51.73; H, 4.22; N, 11.21.

The above compound (3.0 g) is dissolved in 3N HCl (75 ml) with heating. The solution is cooled to room temperature and the resulting precipitate is filtered and washed with ethanol to yield 6,8-difluoro-1-(2-fluoroethyl)-1,4-dihydro-7-(4-hydroxypiperazin-1-yl)-4-oxoquinoline-3-carboxylic acid hydrochloride (1.7 g) as pale yellow needles, m.p. 210°–222° C. (decomposition).

IR (KBr) $\nu$ max (cm$^{-1}$): 3045, 1717, 1620, 1551, 1478, 1280, etc.

NMR (DMSO-d$_6$) $\delta$: 3.00–3.90 (8H, m), 4.50–5.30 (4H, m), 7.90 (1H, dd, J=12 Hz, J=2 Hz), 8.84 (1H, s).

Elementary analysis for $C_{16}H_{16}F_3N_3O$·HCl·H$_2$O: Calcd. (%): C, 45.13; H, 4.50; N, 9.87; Found (%): C, 45.28; H, 4.48; N, 9.76.

EXAMPLE 5

Preparation of
1-cyclopropyl-6,8-difluoro-1,4-dihydro-7-(4-hydroxypiperazin-1-yl)-4-oxoquinoline-3-carboxylic acid 1-Hydroxypiperazine dihydrochloride (4.64 g), triethylamine (8.9 g) and dimethylsulfoxide (25 ml) are added to 1-cyclopropyl-6,7,8-trifluoro-1,4-dihydro-4-oxoquinoline-3-carboxylic acid (5.0 g), which is prepared according to the procidures described in Japanese Patent First Publication No. 212474/1984, and the mixture is stirred with heating at 130° C. for 45 minutes. After cooling of the mixture to room temperature, the resulting crystals are filtered. To the crystals is added water (20 ml) and the mixture is stirred at 50° C. for 1 hour. The insoluble substance is filtered and recrystallized from a mixture of dimethylformamide and water to afford 1-cyclopropyl-6,8-difluoro-1,4-dihydro-7-(4-hydroxypiperazin-1-yl)-4-oxoquinoline-3-carboxylic acid (4.6 g) as pale yellow prisms, m.p. 223°–227° C. (decomposed with foaming).

IR (KBr) $\nu$ max (cm$^{-1}$): 3050, 2840, 1735, 1612, 1560, 1478, 1465, 1320, etc.

NMR (DMSO-d$_6$) $\delta$: 1.10–1.30 (4H, m), 2.42–3.60 (8H, m), 4.10–4.20 (1H, m), 7.64 (1H, dd, J=14 Hz, J=2 Hz), 8.08 (1H, s), 8.50 (1H, s).

Elementary analysis for $C_{17}H_{17}F_2N_3O_4$: Calcd. (%): C, 55.89; H, 4.69; N, 11.50; Found (%): C, 55.90; H, 4.69; N, 11.56.

To the above compound (4.0 g) are added dimethylformamide (100 ml) and 3N HCl (20 ml) and the mixture is heated to dissolve them. The resulting solution is cooled to room temperature, and the resulting crystals are filtered and washed with ethanol to yield 1-cyclopropyl-6,8-difluoro-1,4-dihydro-7-(4-hydroxypiperazin-1-yl)-4-oxoquinoline-3-carboxylic acid hydrochloride (4.0 g) as colorless needles, m.p. 250°–258° C. (decomposition).

IR (KBr) $\nu$ max (cm$^{-1}$): 3040, 3060, 1727, 1713, 1620, 1604, 1513, 1450, 1320, etc.

NMR (DMSO-d$_6$) $\delta$: 1.10–1.30 (4H, m), 3.00–4.00 (9H, m), 7.84 (1H, dd, J=12 Hz, J=3 Hz), 8.68 (1H, s).

Elementary analysis for $C_{17}H_{17}F_2N_3O_4 \cdot HCl$: Calcd. (%): C, 49.30; H, 4.65; N, 10.78; Found (%): C, 49.26; H, 4.66; N, 10.74.

EXAMPLE 6

Preparation of 1-cyclopropyl-6,8-difluoro-1,4-dihydro-7-(4-hydroxypiperazin-1-yl)-4-oxoquinoline-3-carboxylic acid 1-Cyclopropyl-6,8-difluoro-1,4-dihydro-7-(4-hydroxypiperazin-1-yl)-4-oxoquinoline-3-carboxylic acid is prepared by the following procedures (1) and (2).

(1) Preparation of 3-cyano-1-cyclopropyl-6,8-difluoro-1,4-dihydro-7-(4-hydroxypiperazin-1-yl)-4-oxoquinoline:

1-Hydroxypiperazine dihydrochloride (2.45 g) (which is prepared in Preparation 1), dimethylsulfoxide (20 ml) and triethylamine (5.05 g) are added to 1-cyclopropyl-3-cyano-1,4-dihydro-4-oxo-6,7,8-trifluoroquinoline (2.64 g), which is prepared in Preparation 3, and the mixture is stirred with heating at 100° C. for 4 hours. After cooling to room temperature, water (300 ml) is added to the reaction mixture, and the resulting precipitate is filtered and washed with water to afford 3-cyano-1-cyclopropyl-6,8-difluoro-1,4-dihydro-7-(4-hydroxypiperazin-1-yl)-4-oxoquinoline (2.84 g) as pale yellow powder. The powder is recrystallized from dimethylsulfoxide to yield light brown needles, m.p. about 214° C. (decomposition).

IR (KBr) $\nu$ max (cm$^{-1}$): 3332, 3040, 2844, 2228, 1619, 1593, 1478, 1453, 1339, 1330, 1319, 1293, 1269, 1239, etc.

NMR (DMSO-d$_6$) $\delta$: 0.92–1.40 (4H, m), 2.42–2.88 (overlaps with the signal of solvent, 2H, m), 2.88–3.60 (overlaps with the signal of water in solvent, 6H, m), 3.72–4.12 (1H, m), 7.54 (1H, dd, J=12 Hz, J=2 Hz), 8.11 (1H, s), 8.60 (1H, s).

Elementary analysis for $C_{17}H_{16}F_2N_4O_2$: Calcd. (%): C, 58.96; H, 4.66; N, 16.18; Found (%): C, 58.96; H, 4.67; N, 15.93.

(2) Preparation of 1-cyclopropyl-6,8-difluoro-1,4-dihydro-7-(4-hydroxypiperazin-1-yl)-4-oxoquinoline-3-carboxylic acid:

Conc. HCl (30 ml) is added to 3-cyano-1-cyclopropyl-6,8-difluoro-1,4-dihydro-7-(4-hydroxypiperazin-1-yl)-4-oxoquinoline (1.04 g), and the mixture is stirred with heating at 100° C. for 7 hours. The reaction mixture is concentrated to dryness under vacuum to give a pale yellow powdery residue. The residue is washed with water to give 1-cyclopropyl-6,8-difluoro-1,4-dihydro-7-(4-hydroxypiperazin-1-yl)-4-oxoquinoline-3-carboxylic acid hydrochloride (1.04 g) as a pale yellow powder. The infrared spectrum of the product is consistent with that of the 1-cyclopropyl-6,8-difluoro-1,4-dihydro-7-(4-hydroxypiperazin-1-yl)-4-oxoquinoline-3-carboxylic acid hydrochloride obtained in Example 5.

1-Cyclopropyl-6,8-difluoro-1,4-dihydro-7-(4-hydroxypiperazin-1-yl)-4-oxoquinoline-3-carboxylic acid hydrochloride (1.00 g) as prepared above is suspended in water (40 ml). To the suspension is added triethylamine and then the pH of the solution is adjusted to 7.0 with 1N HCl. The resulting precipitate is filtered and washed with water to yield crude 1-cyclopropyl-6,8-difluoro-1,4-dihydro-7-(4-hydroxypiperazin-1-yl)-4-oxoquinoline-3-carboxylic acid (0.85 g) as a colorless powder. The crude product is recrystallized from a mixture of dimethylformamide and water to afford 1-cyclopropyl-6,8-difluoro-1,4-dihydro-7-(4-hydroxypiperazin-1-yl)-4-oxoquinoline-3-carboxylic acid (0.57 g) as pale yellow prisms. The melting point, infrared and nuclear magnetic resonance spectra of this product are consistent with those of 1-cyclopropyl-6,8-difluoro-1,4-dihydro-7-(4-hydroxypiperazin-1-yl)-4-oxoquinoline-3-carboxylic acid obtained in Example 5.

EXAMPLE 7

Tablets each containing 100 mg of 1-ethyl-6-fluoro-1,4-dihydro-7-(4-hydroxypiperazine-1-yl)-4-oxoquinoline-3-carboxylic acid (Compound No. 1 of the invention) are prepared as follows:

(Formula)

| Ingredients | Part by weight |
|---|---|
| The active ingredient (Compound No. 1) | 100 |
| Corn starch | 46 |
| Microcrystalline cellulose | 100 |
| Magnesium stearate | 4 |

(Procedure)

The active ingredient, corn starch and microcrystalline cellulose are mixed with water throughly. The mixture is passed through a sieve to produce granules, which are dried. The granules are mixed with magnesium stearate and the mixture is compressed by a tablet machine to give tablets each weighing 250 mg.

EXAMPLE 8

Granules containing 1-cyclopropyl-6,8-difluoro-1,4-dihydro-7-(4-hydroxypiperazin-1-yl)-4-oxoquinoline-3-carboxylic acid hydrochloride (Compound No. 5 of the invention) are prepared as follows:

(Formula)

| Ingredients | Part by weight |
|---|---|
| The active ingredient (Compound No. 5) | 200 |
| Lactose | 185 |
| Corn starch | 109 |
| Hydroxypropyl cellulose | 6 |

(Procedure)

To a mixture of active ingredient, lactose and corn starch is added a solution of hydroxypropyl cellulose in water (120 ml) and mixed throughly. The mixture is passed through a No. 20 mesh sieve to produce granules. The granules are dried and passed through a sieve of desired size to yield the granules.

EXAMPLE 9

Capsules each containing 100 mg of 1-cyclopropyl-6,8-difluoro-1,4-dihydro-7-(4-hydroxypiperazin-1-yl)-4-oxoquinoline-3-carboxylic acid hydrochloride (Compound No. 5 of the invention) are prepared as follows:
(Formula)

| Ingredients | Part by weight |
|---|---|
| The active ingredient (Compound No. 5) | 100 |
| Corn starch | 60 |
| Lactose | 35 |
| Magnesium stearate | 5 |

(Procedure)

All ingredients are mixed throughly and the resulting powdery mixture is packed into gelatin capsules in an amount of 200 mg.

EXAMPLES 10 TO 13

Tablets each containing 100 mg of 1-cyclopropyl-6-fluoro-1,4-dihydro-7-(4-hydroxypiperazin-1-yl)-4-oxoquinoline-3-carboxylic acid hydrochloride (Compound No. 2 of the invention), 1-ethyl-6,8-difluoro-1,4-dihydro-7-(4-hydroxypiperazin-1-yl)-4-oxoquinoline-3-carboxylic acid hydrochloride (Compound No. 3 of the invention), 6,8-difluoro-1-(2-fluoroethyl)-1,4-dihydro-7-(4-hydroxypiperazin-1-yl)-4-oxoquinoline-3-carboxylic acid hydrochloride (Compound No. 4 of the invention), or 1-cyclopropyl-6,8-difluoro-1,4-dihydro-7-(4-hydroxypiperazin-1-yl)-4-oxoquinoline-3-carboxylic acid hydrochloride (Compound No. 5 of the invention) are prepared by the procedure as described in Example 7 except that Compound No. 2, 3, 4 or 5 is used instead of Compound No. 1 as the active ingredient.

What is claimed is:

1. A quinolinecarboxylic acid compound of the formula:

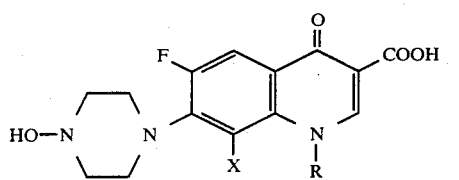

(I)

wherein R is ethyl, 2-fluoroethyl or cyclopropyl, and X is hydrogen atom or fluorine atom, and a pharmaceutically acceptable salt thereof.

2. The compound according to claim 1, wherein R is ethyl and X is hydrogen atom.

3. The compound according to claim 1, wherein R is cyclopropyl and X is hydrogen atom.

4. The compound according to claim 1, wherein R is ethyl and X is fluorine atom.

5. The compounds according to claim 1, wherein R is 2-fluoroethyl and X is fluorine atom.

6. The compound according to claim 1, wherein R is cyclopropyl and X is fluorine atom.

7. An antimicrobial composition which comprises as an active ingredient an effective amount of a compound of the formula (I) as set forth in claim 1 or a pharmaceutically acceptable salt thereof in admixture with a conventional pharmaceutical carrier or diluent.

8. The composition according to claim 7, wherein R is ethyl and X is hydrogen atom.

9. The composition according to claim 7, wherein R is cyclopropyl and X is hydrogen atom.

10. The composition according to claim 7, wherein R is ethyl and X is fluorine atom.

11. The composition according to claim 7, wherein R is 2-fluoroethyl and X is fluorine atom.

12. The composition according to claim 7, wherein R is cyclopropyl and X is fluorine atom.

* * * * *